United States Patent [19]

Prasad et al.

[11] Patent Number: 4,530,664

[45] Date of Patent: Jul. 23, 1985

[54] COBALT-CHROMIUM ALLOYS

[75] Inventors: Arun Prasad, Cheshire; Grant P. Day, Meriden, both of Conn.

[73] Assignee: Jeneric Industries, Inc., Wallingford, Conn.

[21] Appl. No.: 478,832

[22] Filed: Mar. 24, 1983

Related U.S. Application Data

[63] Continuation of Ser. No. 192,335, Sep. 29, 1980, abandoned, which is a continuation-in-part of Ser. No. 93,184, Nov. 13, 1979, abandoned.

[51] Int. Cl.³ ............................................. C22C 19/07
[52] U.S. Cl. ................................... 433/207; 420/436; 420/437
[58] Field of Search ................. 420/436, 437; 433/207

[56] References Cited

U.S. PATENT DOCUMENTS

| | | | |
|---|---|---|---|
| 1,283,264 | 10/1918 | Mowrey . | |
| 2,089,587 | 8/1937 | Tesceda | 32/2 |
| 2,165,849 | 7/1939 | Grossman | 420/436 |
| 2,570,355 | 10/1951 | Low | 75/171 |
| 2,920,956 | 1/1960 | Nisbet et al. | 75/171 |
| 3,134,670 | 5/1964 | Prosen | 75/171 |
| 3,304,177 | 2/1967 | Wlodek | 75/171 |
| 3,399,058 | 8/1968 | Roush | 420/437 |
| 3,413,723 | 12/1968 | Wagner et al. | 32/8 |
| 3,464,817 | 9/1969 | Griffiths | 75/171 |
| 3,667,936 | 6/1972 | Katz | 75/134 N |
| 3,749,570 | 7/1973 | Lyon | 75/171 |
| 3,756,809 | 9/1973 | Asgar | 75/134 F |
| 3,767,391 | 10/1973 | Tuccillo et al. | 75/134 |
| 3,802,875 | 4/1974 | Klein et al. | 75/171 |
| 3,802,934 | 4/1974 | Augustine, Jr. et al. | 148/32.5 |
| 3,819,366 | 6/1974 | Katz | 75/172 R |
| 3,837,838 | 9/1974 | Mohammed | 75/134 |
| 3,914,867 | 10/1975 | Manning et al. | 32/2 |
| 3,981,723 | 9/1976 | Tuccillo | 75/165 |
| 4,007,040 | 2/1977 | Kropp | 75/165 |
| 4,229,215 | 10/1980 | Prosen | 75/134 |
| 4,255,190 | 3/1981 | Prosen | 75/134 |
| 4,263,045 | 4/1981 | Prosen | 75/134 |

FOREIGN PATENT DOCUMENTS

| | | |
|---|---|---|
| 1240671 | 11/1967 | Fed. Rep. of Germany . |
| 1295847 | 3/1969 | Fed. Rep. of Germany . |
| 1608156 | 12/1970 | Fed. Rep. of Germany . |
| 2225577 | 8/1974 | Fed. Rep. of Germany . |
| 2615755 | 12/1976 | Fed. Rep. of Germany . |

OTHER PUBLICATIONS

Ullmann Enzyklopadie der Technischen Chemie, 4th Edition, vol. 10, p. 6 and vol. 14, pp. 281, 282 and 284.

*Primary Examiner*—R. Dean
*Attorney, Agent, or Firm*—Kramer and Brufsky

[57] ABSTRACT

A cobalt-chromium alloy consisting essentially of:

| Element | Weight Percent |
|---|---|
| Cobalt | 50-70 |
| Chromium | 25-35 |
| Molybdenum | 2-10 |
| Manganese | 0-2 |
| Carbon | 0-0.1 | and
(i) from about 1 to about 6% silicon or
(ii) from about 2 to about 6% silicon and from about 0.1 to about 1.5% boron with the proviso that the combined amount of silicon and boron is greater than or equal to 3% or
(iii) from about 1 to about 6% aluminum or
(iv) from about 1 to about 6% silicon and from about 1 to about 6% aluminum with the proviso that the combined amount of silicon and aluminum is less than about 8% or
(v) from about 1 to about 6% silicon, from about 0.1 to about 1.5% boron and from about 1 to about 6% aluminum with the proviso that the combined amount of silicon and aluminum is less than about 8%, said alloy constituents totalling 100%.

These alloys exhibit outstanding physical properties and can be used advantageously as a substitute for precious metals and alloys thereof as well as nickel-chromium-based alloys in the fabrication of porcelain-veneered fixed bridgework and crowns.

5 Claims, No Drawings

COBALT-CHROMIUM ALLOYS

CROSS-REFERENCE TO RELATED APPLICATIONS

This is a continuation of application Ser. No. 192,335, filed Sept. 29, 1980, which in turn is a continuation-in-part of application Ser. No. 093,184, filed Nov. 13, 1979, both now abandoned.

FIELD OF THE INVENTION

This invention relates to cobalt-chromium alloys. More particularly, this invention relates to cobalt-chromium alloys containing silicon and/or aluminum such that the resulting alloys exhibit outstanding physical and thermal properties thereby rendering such alloys suitable for use in the fabrication of porcelain-fused to-metal restorations.

BACKGROUND OF THE INVENTION

Numerous criteria must be met by an alloy to be used in the fabrication of prosthetic dental appliances such as porcelain-veneered fixed bridgework and crowns. The alloy must be tissue tolerant, tarnish resistant, corrosion resistant and non-toxic. In addition, any oxide formed on the alloy surface should be adherent and not grow dramatically in thickness during the porcelain-fixing cycle. The oxides formed must also be compatible with the porcelain, otherwise, they may affect the thermal expansion of the interfacial porcelain. Still further, the oxides should not discolor the porcelain. The alloy must also have a coefficient of thermal expansion slightly higher than that of the porcelains currently available on the market thereby placing the porcelain under compression and minimizing the stresses formed at the interface.

The alloy also should be shape-stable with porcelain application, possess adequate strength for function, produce an acceptable fit and be solderable. Finally, it should possess a high modulus of elasticity, high-yield strength and hardness and be easily cast, ground and polished using techniques conventionally employed in dental laboratories. The criteria which govern the selection of a suitable alloy for use in the preparation of porcelain-veneered fixed bridgework and crowns are quite different from the criteria involved in selecting alloys for use in the fabrication of partial dentures which generally are not used in conjunction with porcelain.

These criteria, to a large extent, have heretofore been met by precious alloys containing gold, platinum, palladium, silver, indium, tin, gallium, zinc, and the like, and trace metals, such as those set forth in U.S. Pat. Nos. 1,283,264, 3,413,723, 3,667,936, 3,767,391, 3,819,366, 3,981,723 and 4,007,040 and the like.

With the ever increasing and fluctuating cost of precious metals and the superior physical properties and technological advantages offered by nickel-chrome-base alloys, such alloys have become widely used as an alternative to precious alloys in dentistry. These alloys generally utilize tin, gallium and the like to impart specific physical characteristics. Typical of such alloys are those described in U.S. Pat. Nos. 2,089,587, 3,304,177, 3,464,817, 3,749,570 and 3,914,867.

Currently, there is growing concern about nickel being an allergen and beryllium being a toxic element. Although much data are still needed, there is an apparent need for a non-precious alloy which contains neither nickel nor beryllium and yet meets the above criteria. A number of cobalt-chromium base alloys with and without nickel and/or beryllium have heretofore been employed in dentistry for the fabrication of removable partials, crowns and bridgework. Typical of such alloys are those described in U.S. Pat. Nos. 3,756,809, 3,802,875, 3,802,934 and 3,837,838. However, their compositions and physical and thermal properties have limited their use for porcelain-veneered crown and bridgework.

Accordingly, it is an object of the present invention to provide a non-precious alloy which exhibits many of the properties of precious metal alloys heretofore considered desirable in the fabrication of porcelain-veneered fixed bridgework and crowns.

It is another object of the present invention to provide a non-precious alloy free of nickel and/or beryllium.

These as well as other objects and advantages are accomplished by the present invention which provides chromium-cobalt alloys which are significantly different from prior chromium-cobalt alloys heretofore employed in the fabrication of prosthetic dental appliances. The chromium-cobalt alloys of the present invention exhibit melting characteristics enabling the use of standard natural gas/oxygen torches conventionally used in dental laboratories. Moreover, the alloys of the present invention exhibit greatly improved oxidation resistance thereby facilitating the formation of a tenacious bond with porcelain. Accordingly, the alloys of the present invention can be successfully employed in the fabrication of porcelain-veneered fixed bridgework and crowns in lieu of the precious metal and nickel-chromium-base alloys heretofore employed.

The cobalt-chromium alloys of the present invention consist essentially of:

| Element | Weight Percent |
| --- | --- |
| Cobalt | 50–70 |
| Chromium | 25–35 |
| Molybdenum | 2–10 |
| Manganese | 0–2 |
| Carbon | 0–0.1 | and (i) from about 1 to about 6% silicon or (ii) from about 2 to about 6% silicon and from about 0.1 to about 1.5% boron with the proviso that the combined amount of silicon and boron is greater than or equal to 3% or (iii) from about 1 to about 6% aluminum or (iv) from about 1 to about 6% silicon and from about 1 to about 6% aluminum with the proviso that the combined amount of silicon and aluminum is less than about 8% or (v) from about 1 to about 6% silicon, from about 0.1 to about 1.5% boron and from about 1 to about 6% aluminum with the proviso that the combined amount of silicon and aluminum is less than about 8%, said alloy constituents totalling 100%.

These alloys exhibit outstanding physical properties and can be used advantageously as a substitute for precious metals and alloys thereof as well as nickel-chromium-based alloys in the fabrication of porcelain-veneered fixed bridgework and crowns.

In addition, the alloy can contain yttrium and/or zirconium to improve the grain structure and the grain boundary characteristics. The alloy can contain yttrium and/or zirconium, either alone or in combination, in an amount up to about 0.25%.

Preferably, the cobalt-chromium alloys of the present invention consist essentially of:

| Element | Percent by Weight |
|---|---|
| Cobalt | 55–65 |
| Chromium | 25–35 |
| Molybdenum | 2–6 |
| Manganese | 0.5–2 |
| Carbon | 0–0.1 | and
(i) from about 2 to about 4.5% silicon or
(ii) from about 2 to about 4.5% silicon and from about 0.5 to about 1% boron with the proviso that the combined amount of silica and boron is at least 3.5% or
(iii) from about 2 to about 4.5% aluminum or
(iv) from about 2 to 4.5% silicon and from about 2 to 4.5% aluminum with the proviso that the combined amount of silicon and aluminum is less than 8% or
(v) from about 2 to about 4.5% silicon, from about 0.25 to about 1% boron and from about 2 to about 4.5% aluminum with the proviso that the combined amount of silicon and aluminum is less than about 8%, said alloy constituents totalling 100%.

It has been found in accordance with the present invention that the amounts of silicon, boron and/or aluminum employed in the present cobalt-chromium alloys are critical in meeting the various criteria imposed on alloys which are useful in the preparation of porcelain-veneered fixed bridgework and crowns.

Thus, it has been found that if silicon is used in the absence of boron, it can be employed in amounts varying from about 1 to 6% by weight of the total alloy. Amounts less than 1% silicon do not provide the requisite deoxidation effects nor would the requisite lower melting range be obtained. If silicon is present in amounts in excess of about 6%, the resulting alloy exhibits lower physical properties and becomes too brittle for use in a fixed dental appliance. Preferably, silicon is employed in amounts ranging from about 2 to about 4.5%.

If boron is used in conjunction with silicon, it has been found that for up to 2% silicon, boron in amounts greater than trace amounts and up to 1% boron results in significant and undesirable sparking and pyrotechnics when the alloy is melted using a standard natural gas-/oxygen torch as commonly used in dental laboratories. The sparking and pyrotechnics can be avoided by employing silicon and boron in combined amounts of greater than or equal to 3% with silicon being present in a minimum amount of about 2%. If boron is present in amounts greater than about 1.5%, the resulting alloy is extremely difficult to machine and polish by conventional techniques used in a dental laboratory. Preferably, when silicon and boron are used in combination, the silicon ranges from about 2 to about 4.5% and the boron ranges from about 0.5 to about 1%.

It has been further found that when silicon is employed in the absence of boron in an amount of at least 3.5% or silicon and boron are used in combination in an amount of at least 3.5% with the silicon being present in an amount from about 2 to about 4.5% silicon, then the resulting alloys surprisingly melt very much like a precious metal alloy and exhibit melting characteristics which allow the alloy ingots to merge together or "puddle" as do precious metal alloys upon melting. Accordingly, the melting and casting of these alloys is more easily performed by laboratory technicians who are accustomed to working with precious metal alloys.

When aluminum is used in lieu of silicon, the resulting alloy is lower melting but the surface tension of the molten ingot is such that it does not "puddle" or merge with adjacent ingots as do the precious metal alloys. Moreover, porcelain readily and firmly bonds to the alloys of the present invention which contain a relatively high aluminum content; whereas, it has been found that porcelain forms an adequate bond with the alloys of the present invention containing silicon or relatively low levels of aluminum. It is considered preferable, in the latter instances, to form an aluminide coating on the alloy castings prior to application of the porcelain thereby enhancing the resulting bond. The aluminide coating can be applied by conventional techniques such as the slurry technique described in "the Superalloys" edited by C. T. Sims et al, pages 346–359, John Wiley & Sons, New York (1072). The adhesion between the so-coated alloy surface and porcelain has been found to be excellent.

The cobalt-chromium alloys of the present invention are especially suited for use in the fabrication of prosthetic dental appliances since the cobalt in the alloy imparts characteristics to the alloy which closely correspond with that of precious metals, especially the coefficient of thermal expansion which is quite close to that of gold. The chromium in the alloy provides enhanced corrosion and tarnish resistance. Chromium in amounts of from about 25% to 35% and also the molybdenum in amounts of from about 2% to 10% act as solid solution strengtheners and provide a convenient means of adjusting the thermal expansion characteristics of the alloy to conform to the variations encountered upon use of different commercial porcelains. In the presence of chromium, it has been found that amounts of molybdenum in excess of 10% results in undesirable brittleness. Manganese can be included in the alloy in amounts of from 0 to about 2% to act as a desulfurizing agent. In order to essentially reduce carbide formation, it is preferred that the carbon content be kept as low as possible and preferably below 0.1%. It has been found that the presence of carbon in amounts in excess of 0.1% can result in deleterious bubble formation under the porcelain veneer of the fixed dental appliance.

Moreover, if desired, it has been found that tin can be employed in amounts up to about 20% by weight to obtain a further lowering of the melting point. Also, the cobalt content of the alloy can be reduced, if desired, without adverse effect, through replacement with up to about 6% by weight of iron.

It has been found that silicon, boron and aluminum effect a lowering of the casting temperature and enhance the oxidation resistance of the alloy. The inclusion of yttrium and/or zirconium in the alloys of the present invention is optional in amounts of from 0 to about 0.25%. These elements function to fill lattice discontinuities that may exist at grain boundaries and thereby increase structural perfection.

The castings obtained with the alloys of the present invention exhibit smooth, less porous surfaces than heretofore obtainable. Moreover, the lower casting temperatures now obtainable result in less interaction with the commercially available investments thereby enabling the fabrication of less porous castings.

The alloys of the present invention exhibit a melting range of from about 2200° F. to about 2500° F.; a coefficient of thermal expansion ranging from about $13 \times 10^6$ in/in°C. to about $15 \times 10^6$ in/in°C., which is slightly higher than that of the porcelains currently available, thereby placing the porcelain under compression and minimizing stress at the interface; a yield strength in excess of about 60,000 psi; an ultimate tensile strength in excess of about 75,000 psi and an elongation in excess of about 3%.

The alloys of the present invention can be prepared by conventional alloying techniques. If desired, alloying can be effected in air, under vacuum or by employing a blanket of an inert gas such as argon. The latter precautions, although preferred, are not considered essential. Generally, the major alloy constituents are melted first, such as through use of an induction furnace, taking care to maintain a homogeneous distribution of chromium in the melt by overcoming its tendency to float to the surface. After the cobalt and chromium have been melted and are well dispersed, molybdenum can be added. Thereafter, the remaining alloy constituents can be added in either elemental form or as a preformed alloy with cobalt or chromium. Thus, for example, it is advantageous to add boron as a cobalt-boron alloy. Once the alloy melt is prepared and ingots cast therefrom, the remelting of the alloy ingot may be accomplished using a standard natural gas/oxygen torch or induction melting equipment.

The alloys of the present invention can be used instead of precious metals and nickel-chrome-base alloys without requiring any significant changes in technique other than as presently practiced in a dental laboratory. The absence of nickel and beryllium precludes the need for any special handling precautions.

The following examples further illustrate the criticalities of the alloy composition of the present invention. Unless otherwise specified, all percentages and parts are by weight.

EXAMPLES 1-7

The alloy compositions set forth in Table I were prepared in the manner set forth above:

TABLE I

| Alloy | Co | Cr | Mo | Mn | Si |
|---|---|---|---|---|---|
| 1 | 60.4 | 30.5 | 4.5 | 1.0 | 3.5 |
| 2 | 62.4 | 30.0 | 2.0 | 1.0 | 4.0 |
| 3 | 62.4 | 30.0 | 2.0 | 0.75 | — |
| 4 | 60.25 | 30.0 | 4.0 | 0.50 | 5.0 |
| 5 | 60.0 | 32.0 | 3.0 | 0.75 | 2.0 |
| 6 | 64.4 | 28.0 | 2.5 | 0.75 | 1.0 |
| 7 | 62.5 | 30.0 | 2.5 | 0.75 | 3.5 |

| Alloy | C | B | Al | Y | Zr |
|---|---|---|---|---|---|
| 1 | <0.1 | — | — | — | — |
| 2 | <0.1 | 0.50 | — | — | — |
| 3 | <0.1 | — | 4.0 | Y + Zr = 0.25 | |
| 4 | <0.1 | 0.15 | — | — | — |
| 5 | <0.1 | 0.25 | 2.0 | — | — |
| 6 | <0.1 | — | 3.0 | 0.25 | — |
| 7 | <0.1 | — | 0.5 | — | 0.25 |

Alloys 1, 2, 4 and 7 were found to melt readily when heated in a ceramic crucible with a standard natural gas/oxygen torch and ingots thereof were found to "puddle" and pour easily. Alloys 3, 5 and 6 melted readily but ingots thereof did not "puddle"; instead, they retained their independent ingot structure even in molten condition. Alloys 1-7 were all found suitable for use in fabricating and constructing prosthetic dental devices such as fixed bridges and crowns.

EXAMPLES 8-18

The alloy compositions set forth in Table II were prepared in the manner set forth hereinabove. These alloys were prepared to further exemplify the present invention and to illustrate the criticality of the ranges of various of the elements contained therein.

TABLE II

| | Composition | | | | | |
|---|---|---|---|---|---|---|
| | Co | Cr | Mo | Mn | Si | B |
| 1 | 61.5 | 30.0 | 2.5 | 1.0 | 1.0 | 1 |
| 2 | 63.0 | 30.0 | 2.5 | 1.0 | 1.0 | 2.5 |
| 3 | 63.0 | 30.0 | 2.5 | 1.0 | 2.5 | 1 |
| 4 | 62.0 | 30.0 | 2.5 | 1.0 | 1 | 3.5 |
| 5 | 60.5 | 30.0 | 2.5 | 1.0 | 1 | 5.0 |
| 6 | 63.0 | 30.0 | 2.5 | 1.0 | 2 | 1.5 |
| 7 | 64.5 | 30.0 | 2.5 | 1.0 | 2 | 0 |
| 8 | 60.5 | 30.0 | 5.0 | 1.0 | 2.5 | 1.0 |
| 9 | 61.75 | 30.0 | 5.0 | 1.0 | 2.0 | .25 |
| 10 | 61.50 | 30.0 | 5.0 | 1.0 | 2.0 | .5 |
| 11 | 61.00 | 30.0 | 5.0 | 1.0 | 2.5 | .5 |

The alloys shown in Table II were tested to determine their physical properties and their suitability for use in the production of dental castings, especially in terms of their melting, casting, polishing and machinability characteristics. Table III summarizes the physical properties obtained and the melting and polishing characteristics.

TABLE III

| | Physical Properties | | | |
|---|---|---|---|---|
| Alloy | Y.S. (× 1000) | U.T.S. (× 1000) | Elongation % | Polishing Characteristics |
| 1 | Excessive sparking during melting | | | Easy |
| 2 | 90 | 90 | 3.5 | Difficult |
| 3 | 105 | 126 | 6.8 | Relatively Easy |
| 4 | 73 | 73 | 2.6 | Extremely Difficult |
| 5 | 53 | 53 | 2.0 | Extremely Difficult |
| 6 | 118 | 128 | 5.5 | Relatively Easy |
| 7 | 35 | 66 | 10.0 | Very Easy |
| 8 | 110 | 110 | 4.0 | Relatively Easy |
| 9 | Excessive sparking during melting | | | Easy |
| 10 | Excessing sparking during melting | | | Easy |
| 11 | 52 | 52 | 3.0 | Easy |

Y.S. = Yield Strength (psi)
U.T.S. = Ultimate Tensile Strength (psi)

A. Melting Characteristics

The melting characteristics of the alloys were determined by observation thereof under the action of a natural gas/oxygen torch generally used in the dental laboratory. Alloys 1, 9 and 10 puddle sluggishly and produce violent sparking reactions during melting. In addition, there is a significant amount of gaseous absorption. The relative fluidity of the alloys listed in Table II can be expressed as follows:

Alloy 5>4>2>6>3>8>11>10>9>1>7

B. Casting Characteristics

The casting characteristics are based on observations of the casting ability of the molten alloy employing the typical investment casting procedures and equipment employed in the dental industry. The relative castability of the alloys listed in Table II can be expressed as follows:

Alloy 3=6=7=8=11>5>4>2>9=10=1

All of the above alloys other than alloys 3, 6, 7, 8, and 11 exhibit casting characteristics which are not acceptable for dental fixed bridgework.

C. Machinability

The machinability characteristic is based upon the ease with which the alloy can be machined with the equipment typically used in the dental industry. The relative ease with which the alloys listed in Table II can be machined can be expressed as follows:

Alloy 7>9=10>11>3=8>6>1>2>4>5

From the foregoing, it can readily be seen that only those alloys meeting the critical criteria of the instant invention (alloys 3, 6, 7, 8 and 11) are suitable for use in the manufacture of dental fixed bridgework and crowns.

What is claimed is:

1. A porcelain-fused-to-metal dental restoration comprising porcelain fused to a casting of a cobalt-chromium alloy consisting essentially of:

| Element | Weight Percent |
|---|---|
| Cobalt | 50–70 |
| Chromium | 25–35 |
| Molybdenum | 2–10 |
| Manganese | 0–2 |
| Carbon | 0–0.1 | and
(i) from about 3.5 to about 6% silicon, or
(ii) from about 2 to about 6% silicon and from about 0.1 to 1.5% boron with the proviso that the combined amount of silicon and boron is greater than or equal to 3%, or
(iii) from about 1 to about 6% aluminum, or
(iv) from about 1 to about 6% silicon and from about 1 to about 6% aluminum with the proviso that the combined amount of silicon and aluminum is less than about 8%, or
(v) from about 1 to about 6% silicon, from about 0.1 to about 1.5% boron and from about 1 to about 6% aluminum with the proviso that the combined amount of silicon and aluminum is less than about 8%, the named alloy constituents totalling 100%.

2. A porcelain-fused-to metal dental restoration as defined in claim 1 additionally containing yttrium and/or zirconium, either alone or in combination, in an amount up to about 0.25 weight percent.

3. A porcelain-fused-to metal dental restoration as defined in claim 1 additionally containing up to about 20 weight percent tin.

4. A porcelain-fused-to metal dental restoration as defined in claim 1 additionally containing up to about 6 weight precent iron.

5. A porcelain-fused-to-metal dental restoration comprising porcelain fused to a casting of a cobalt-chromium alloy consisting essentially of:

| Element | Weight Percent |
|---|---|
| Cobalt | 55–65 |
| Chromium | 25–35 |
| Molybdenum | 2–6 |
| Manganese | 0.5–2 |
| Carbon | 0–0.1 |

(i) from about 3.5 to about 4.5% silicon, or
(ii) from about 2 to about 4.5% silicon and from about 0.5 to about 1% boron with the proviso that the combined amount of silicon and boron is at least 3.5%, or
(iii) from about 2 to about 4.5% aluminum, or
(iv) from about 2 to 4.5% silicon and from about 2 to 4.5% aluminum with the proviso that the combined amount of silicon and aluminum is less than 8%, or
(v) from about 2 to about 4.5% silicon, from about 0.25 to about 1% boron and from about 2 to about 4.5% aluminum with the proviso that the combined amount of silicon and aluminum is less than about 8%, the named alloy constituents totalling 100%.

* * * * *